United States Patent
Piron et al.

(10) Patent No.: US 11,119,171 B2
(45) Date of Patent: Sep. 14, 2021

(54) SYSTEMS AND METHODS FOR ADAPTIVE MULTI-RESOLUTION MAGNETIC RESONANCE IMAGING

(71) Applicant: SYNAPTIVE MEDICAL INC., Toronto (CA)

(72) Inventors: Cameron A. Piron, Toronto (CA); Jeff Stainsby, Toronto (CA); Chad Harris, Toronto (CA); Philip Beatty, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 0 days.

(21) Appl. No.: 15/745,169

(22) PCT Filed: Jul. 16, 2015

(86) PCT No.: PCT/IB2015/055407
§ 371 (c)(1),
(2) Date: Jan. 16, 2018

(87) PCT Pub. No.: WO2017/009691
PCT Pub. Date: Jan. 19, 2017

(65) Prior Publication Data
US 2018/0210053 A1    Jul. 26, 2018

(51) Int. Cl.
*G01R 33/54* (2006.01)
*G01R 33/561* (2006.01)
(Continued)

(52) U.S. Cl.
CPC .......... *G01R 33/543* (2013.01); *A61B 5/0037* (2013.01); *A61B 5/035* (2013.01);
(Continued)

(58) Field of Classification Search
CPC ....... A61B 5/0037; A61B 5/035; A61B 5/037; A61B 5/055; A61B 5/7285; G01R 33/543;
(Continued)

(56) References Cited

U.S. PATENT DOCUMENTS

2003/0095150 A1* 5/2003 Trevino ............... G01R 33/546
715/810
2007/0103155 A1* 5/2007 Tsekos ............... G01R 33/4824
324/307
(Continued)

FOREIGN PATENT DOCUMENTS

| WO | 2014139022 | 9/2014 |
|----|------------|--------|
| WO | 2014139023 | 9/2014 |
| WO | 2014139024 | 9/2014 |

OTHER PUBLICATIONS

Gaggl et al., "High-Resolution Reduced Field of View Diffusion Tensor Imaging Using Spatially Selective RF Pulses," Magnetic Resonance in Medicine 72:1668-1679 (2014).
(Continued)

*Primary Examiner* — Rishi R Patel

(57) ABSTRACT

Systems and methods for adaptive, multi-resolution magnetic resonance imaging ("MRI"), in which an MRI scan prescription is adaptively changed to acquire high-quality data from select regions-of-interest ("ROI") in a larger field-of-view ("FOV"), are provided. The higher quality data can include data representing higher spatial resolution, higher signal-to-noise ratio ("SNR"), increased diffusion encoding via repeated acquisition with a larger number of diffusion-encoding directions, and so on. A composite image can be generated that displays the higher quality images of the ROIs overlaid on the larger FOV.

19 Claims, 3 Drawing Sheets

(51) Int. Cl.
*A61B 5/055* (2006.01)
*A61B 5/00* (2006.01)
*A61B 5/03* (2006.01)
*G01R 33/563* (2006.01)

(52) U.S. Cl.
CPC .............. *A61B 5/037* (2013.01); *A61B 5/055* (2013.01); *G01R 33/561* (2013.01); *G01R 33/56341* (2013.01); *A61B 5/7285* (2013.01)

(58) Field of Classification Search
CPC .............. G01R 33/561; G01R 33/5608; G01R 33/5604; G01R 33/56341
See application file for complete search history.

(56) References Cited

U.S. PATENT DOCUMENTS

| 2007/0276220 | A1  | 11/2007 | Harvey      |            |
|---|---|---|---|---|
| 2010/0189328 | A1  | 7/2010  | Boemert     |            |
| 2010/0329528 | A1* | 12/2010 | Hajnal      | A61B 5/055 |
|              |     |         |             | 382/131    |
| 2011/0105884 | A1  | 5/2011  | Beck        |            |
| 2011/0286630 | A1  | 11/2011 | Harder      |            |
| 2012/0112743 | A1  | 5/2012  | Granlund    |            |
| 2012/0112748 | A1  | 5/2012  | Hetherington|            |
| 2013/0094743 | A1  | 4/2013  | Coenegrachts|            |
| 2013/0278257 | A1* | 10/2013 | Boada       | G01R 33/56341 |
|              |     |         |             | 324/309    |
| 2015/0084627 | A1* | 3/2015  | Ruhm        | G01R 33/385 |
|              |     |         |             | 324/309    |
| 2015/0260811 | A1* | 9/2015  | Blumhagen   | G01R 33/3875 |
|              |     |         |             | 324/309    |
| 2016/0069975 | A1* | 3/2016  | Rothberg    | G01R 33/3854 |
|              |     |         |             | 324/322    |

OTHER PUBLICATIONS

International Search Report and Written Opinion issued in corresponding International Application No. PCT/IB2015/055407, dated Oct. 28, 2015, 7 pages.

Landman et al., "Compressed Sensing of Multiple Intra-Voxel Orientations with Traditional DTI," Med Image Comput Comput Assist Interv. 2008 ; 2008: 175-182.

Li et al., "Compressed Sensing Diffusion Tensor Imaging (DTI) with Tensor and Phase Constraints," Proc. Intl. Soc. Mag. Reson. Med. 19 (2011) pp. 2840.

Plenge et al., "Super-Resolution Methods in MRI: Can They Improve the Trade-Off Between Resolution, Signal-to-Noise Ratio, and Acquisition Time?" Magnetic Resonance in Medicine 68:1983-1993 (2012).

* cited by examiner

SYSTEMS AND METHODS FOR ADAPTIVE MULTI-RESOLUTION MAGNETIC RESONANCE IMAGING

CROSS-REFERENCE TO RELATED APPLICATIONS

This application represents the national stage entry of PCT International Application PCT/IB2015/055407, filed Jul. 16, 2015. The contents of this application are hereby incorporated by reference as set forth in their entirety herein.

BACKGROUND OF THE INVENTION

The field of the invention is systems and methods for magnetic resonance imaging ("MRI"). More particularly, the invention relates to systems and methods for adaptive, multi-resolution MRI.

MR imaging typically takes a relatively long amount of time relative to other imaging modalities. In addition there is normally a direct correlation between improving the MR image quality and the amount of time required to improve the image quality. This is due to both the fact that MR image data has to be collected in multiple repeat acquisitions with MR signal recovery between acquisitions; and also because each MR data sample represents a single point in k-space which contributes information to all points in image space. Thus to improve the image quality, even in a small region, normally involves improving the entire volume of k-space.

In many MR imaging applications, a lower-quality image volume can be used to identify regions of greater relevance that would benefit from higher quality data. In traditional methods, the only way to obtain this higher quality data is to re-image the entire volume with a higher quality (e.g., higher spatial resolution, higher signal to noise, etc) scan, which requires greater scanning time than the original lower-quality image. There thus remains a need for an MRI technique that is capable of acquiring high quality images of localized regions in a time-optimized manner and without needing to re-image an entire field-of-view.

SUMMARY OF THE INVENTION

The present invention overcomes the aforementioned drawbacks by providing a method for adaptive magnetic resonance imaging ("MRI") using an MRI system. An image of a subject acquired with a medical imaging system (e.g., an MRI system, a CT system, an optical imaging system) is provided. At least one region-of-interest ("ROI") is identified in the provided image. The ROI is identified for a region where a higher quality image than the provided image is desired. Scan parameters that define how to control the MRI system to acquire data from the at least one ROI are then determined, and data are acquired from the at least one ROI using the determined scan parameters to control the MRI system to provide radio frequency ("RF") excitation to substantially only the at least one ROI. An image of the at least one ROI is reconstructed from the data acquired from the ROI, and this reconstructed image depicts the ROI with a higher image quality than the provided image. Higher image quality can include higher spatial resolution, higher signal-to-noise ratio ("SNR"), or increased angular resolution for diffusion imaging through repeated imaging with a large number of different diffusion-encoding directions.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
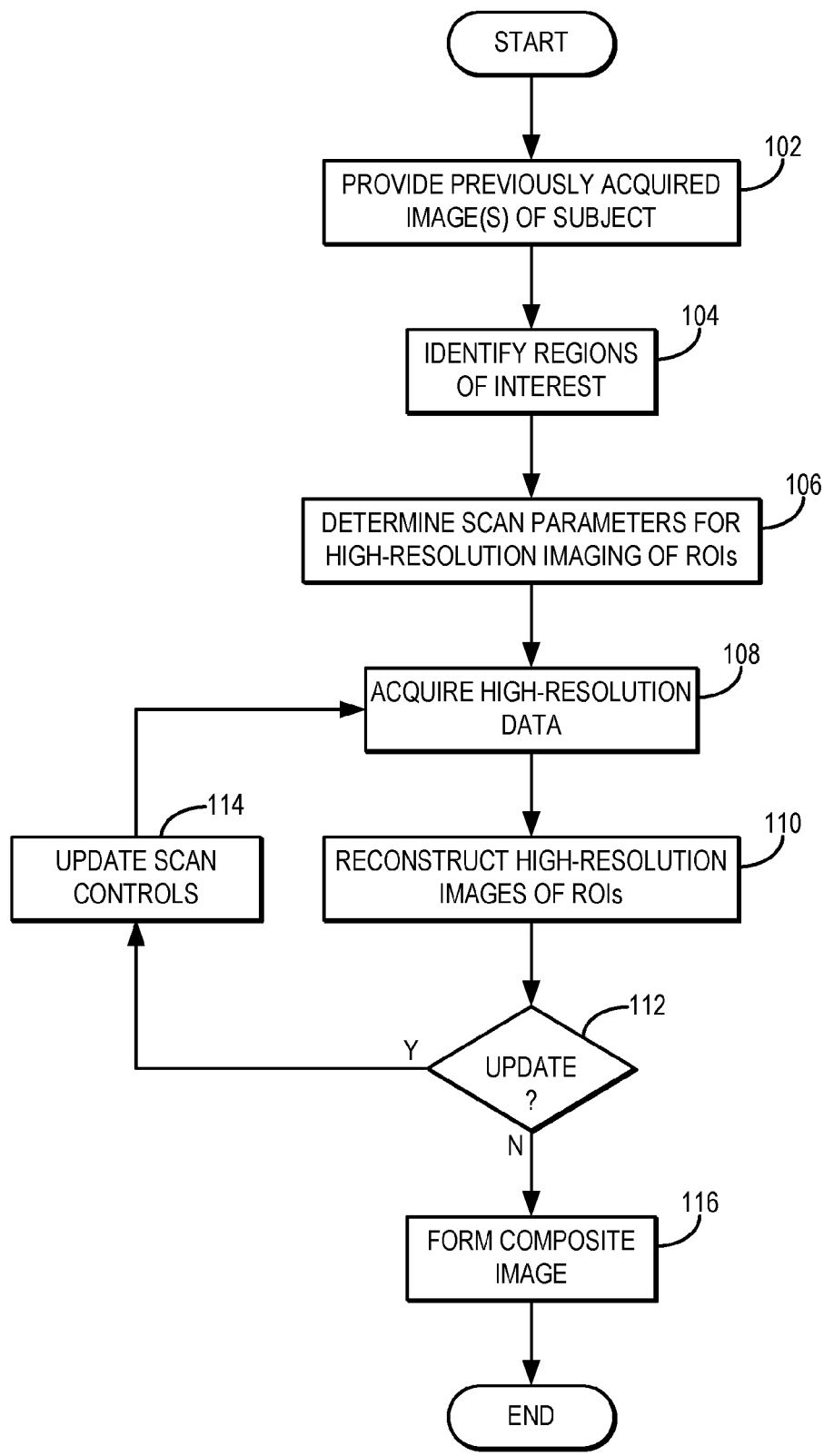
FIG. 1 is a flowchart setting forth the steps of an example method for adaptive, multi-resolution magnetic resonance imaging ("MRI")

Described here are systems and methods for adaptive, multi-resolution magnetic resonance imaging ("MRI"), in which an MRI scan prescription is adaptively changed to acquire high-resolution data from select regions-of-interest ("ROI") in a larger field-of-view ("FOV").

As an example, a lower-quality imaging volume is acquired and from this volume one or more spatially localized ROIs where higher quality data is desired are identified based on prior information. Additional data is then acquired only from these identified ROIs using multidimensional signal localization to localize magnetic resonance signals to the smaller ROIs. As one example, multidimensional signal localization may include using multidimensional spatially localized signal excitations such that magnetic resonance signals are generated only in the ROIs excited by the localized RF excitations. As another example, multidimensional signal localization may include using adaptive shim coils to perturb the magnetic field such that coherent signal excitation is achieved only in the localized ROIs. Information from these ROIs can be acquired and encoded in time much more efficiently because of their reduced spatial extent. The information from these additional acquisitions can be merged with the original data to produce composite image data with lower quality information in some regions and higher quality information in the more relevant ROIs that have been identified.

Some approaches exist to perform higher quality imaging over reduced spatial volumes. These methods are generally referred to as reduced field-of-view ("rFOV") imaging techniques. In these rFOV methods, the rFOV imaging data are acquired in a separate image acquisition and the rFOV images are evaluated and viewed as independent images from any full FOV approaches.

The methods described here, however, can produce composite data sets that have relevant information from both lower-quality, large FOV data and higher-quality, local ROI data, and can acquire these data in a time-optimized manner. Furthermore, rFOV imaging approaches image a single volume of reduced spatial extent, but the methods described here are capable of multidimensional signal localization to simultaneously generate and acquire magnetic resonance signals from more than one spatially localized volume. For instance, the methods described here can utilize modulated, multidimensional RF pulses to simultaneously excite more than one spatially localized volume. In some other instances, adaptive shim coils may be used to perturb the magnetic field to achieve coherent signal excitation more than one spatially localized volume.

A related idea of combining multiple low-resolution image sets into a single higher-resolution or higher-quality data set has also been demonstrated. This imaging technique is commonly called a "super resolution" approach. These super resolution approaches require two-dimensional imaging data and are not applied to three-dimensional data acquisitions, which are more typically performed in clinical brain imaging. Furthermore, super resolution imaging techniques have been presented as a means to improve spatial resolution in a time-efficient or SNR-efficient manner in the slice-direction only. The methods described here, however, can be generalized to improving data quality in multiple dimensions and can be applied to three-dimensional imaging methods.

Referring now to FIG. 1, a flowchart is illustrated as setting forth the steps of an example method for adaptive, multi-resolution MRI. The method includes providing previously acquired images of the subject, as indicated at step 102. These previously acquired images can be include magnetic resonance images, or images obtained with other imaging modalities.

As one example, the previously acquired images can include low-resolution magnetic resonance images. These images can be previously acquired from the subject and thus retrieved from data storage, or these images can be acquired from the subject during the same imaging session. For instance, the low-resolution images can be acquired as part of the volume scan prescription. As another example, the previously acquired images can include images obtained by imaging modalities other than MRI, such as optical imaging provided by optical guidance during surgical interventions.

Based on the provided images of the subject, regions-of-interest ("ROIs") for which higher resolution imaging is desired are identified, as indicated at step 104. As one example, the ROIs can be identified by a user. For instance, the ROIs could be manually drawn regions that encompass areas of which a clinician would be interested in obtaining higher quality images. The ROIs could thus be drawn to encompass a tumor or other pathology. As another example, the ROIs can be semi-automatically or automatically determined. For instance, the ROIs could be determined based on a segmentation algorithm, or by identifying regions having certain image contrast characteristics.

Scan parameters for each identified ROI are then determined, as indicated at step 106. As one example, the scan parameters for a given ROI define a spatially-tailored RF excitation that will predominantly deliver RF energy only to that ROI. As another example, the scan parameters can include those scan parameters that will result in higher resolution images being obtained for the limited spatial extent of the ROIs. For instance, the scan parameters can define a higher spatial resolution, a higher angular resolution for diffusion imaging (e.g., a larger number of diffusion-encoding directions), and so on. In this manner, higher resolution data can then be acquired from each ROI using the scan parameters determined for each given ROI, as indicated at step 108. High-resolution images are then reconstructed for each ROI from the data acquired for each given ROI, as indicated at step 110.

A determination is then made at decision block 112 whether the scan parameters for any given ROI should be updated to provide a higher quality image. As one example, it may be determined that a higher quality image can be generated by changing the spatial extent of the spatially-tailored RF excitation. If it is determined that the scan parameters should be updated, then the parameters are so updated at step 114 and new data are acquired from the relevant ROIs. Images are then reconstructed from the new data and the determination made once again whether further updates are needed.

Figure 2:
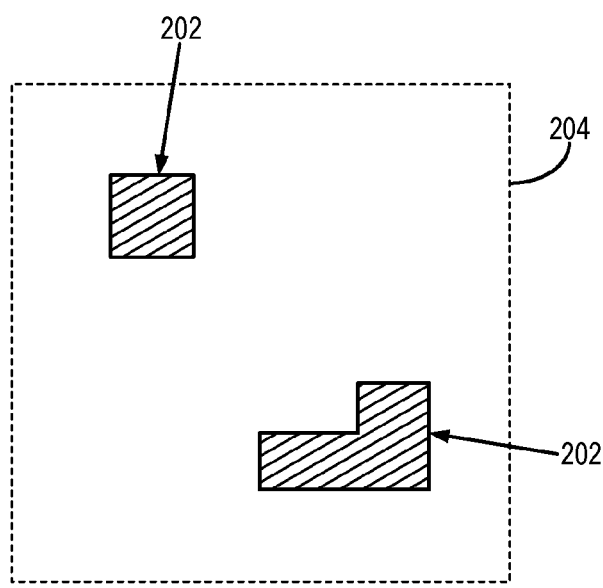
FIG. 2 is an example of a composite image that combines high quality images of local regions with a lower quality image of a full field-of-view.

If no updates are needed, then the method proceeds at step 116 by forming one or more composite images; however, in some embodiments the ROI images can be stored without using them to form a composite image. In general, a composite image includes overlying the high resolution ROI images on top of a lower resolution image of the entire FOV. For example, the composite image can include overlaying the ROI images on top of the previously acquired images of the subject. An example of such a composite image is illustrated in FIG. 2, in which higher quality images of local ROIs 202 are displayed as overlaid on a lower quality image of the entire FOV 204.

The composite image can also be generated as a dynamic display element, in which an image of the entire FOV is displayed, but through user interaction a pop-up or overlay of the higher resolution ROI images can be displayed. For example, the composite image can include displaying an image of the entire FOV and when a user moves a cursor into a region associated with one of the ROI images, the ROI image can be displayed in a pop-up or otherwise overlaid on the image of the entire FOV. In this manner, the information contained in the higher-resolution ROI images can be accessed and displayed without confounding the display image of the entire FOV, which can provide context.

As one example implementation of the method described above, the adaptive multi-resolution imaging can be used for diffusion imaging. In this example, the previously acquired images of the subject can include diffusion-weighted images acquired with common parameters, such as 2 mm isotropic resolution and a limited number of diffusion-encoding directions (e.g., 6 or 25). Using images acquired with these common parameters may not provide sufficient angular resolution for performing diffusion tractography in areas where significant fiber crossing occurs, where edema is present, or where smaller fiber bundles are located.

However, these regions can be identified as ROIs for which higher angular resolution diffusion-weighted images can be obtained. For instance, additional information can be acquired from the local volumes of interest that encompass the identified ROIs. As one example, this additional information can be acquired using multidimensional signal localization, which may include using multidimensional excitation pulses (e.g., either via multiple repeat acquisitions of each local volume, one at a time, or via excitation pulses that can excite multiple local regions simultaneously), or using adaptive shim coils to perturb the magnetic field such that coherent signal excitation is limited to the identified ROIs. As another example, this additional information could be acquired using the same spatial resolution as the underlying images, but using many more diffusion directions to increase the angular resolution of the diffusion imaging. As still another example, the additional information could be acquired using the same spatial resolution and same diffusion directions, but by using additional averages to improve the signal-to-noise ratio ("SNR") of the data in the identified regions. As still another example, the additional information could be acquired using the same spatial resolution, but by using multiple different b-values.

As another example implementation of the method described above, the adaptive multi-resolution imaging can be used for low-field visualization of a particular anatomical region, such as the subthalamic nucleus ("STN"). In this example, the previously acquired images can include a contrast-optimized 3D image volume of a large brain volume that encompasses the STN. For instance, the contrast-optimized imaging sequence can be optimized for $T_1$ and $T_2^*$ contrast at operating field strength for maximal contrast in the STN region. Local regions where STN should reside can then be localized in this image volume, and these local regions identified as ROIs for additional, targeted imaging. Reduced volume-of-interest imaging can then be used to acquire higher quality imaging data over the identified STN regions, and the higher quality imaging data could then be merged with the full volume images to generate composite images containing large volume context imaging with high quality local information.

As another example implementation of the method described above, adaptive multi-resolution imaging can be used for tracking medical devices, surgical tools, and the like during an interventional procedure. As described above, images can be provided from an optical imaging system, such as one that may be used during an interventional procedure, or from a surgical navigation system. These images can then be used to define the ROIs for higher resolution magnetic resonance imaging. To this end, Advantageously, this approach can utilize lower quality images that are more quickly acquired to provide large volume contextual information during an interventional procedure, but the localized ROI images can be acquired to more accurate, localized information relevant to the interventional procedure. This approach therefore provides an overall reduction in scan time because only the localized ROI images need to be higher quality, which can improve the efficiency and accuracy of the interventional procedure.

As another example implementation of the method described above, adaptive multi-resolution imaging can be used to reduce artifacts, such as those artifacts associated with differences in magnetic susceptibility. For instance, the voxel size around a metallic implant can be reduced to provide less distortion in the localized ROI images.

Figure 3:
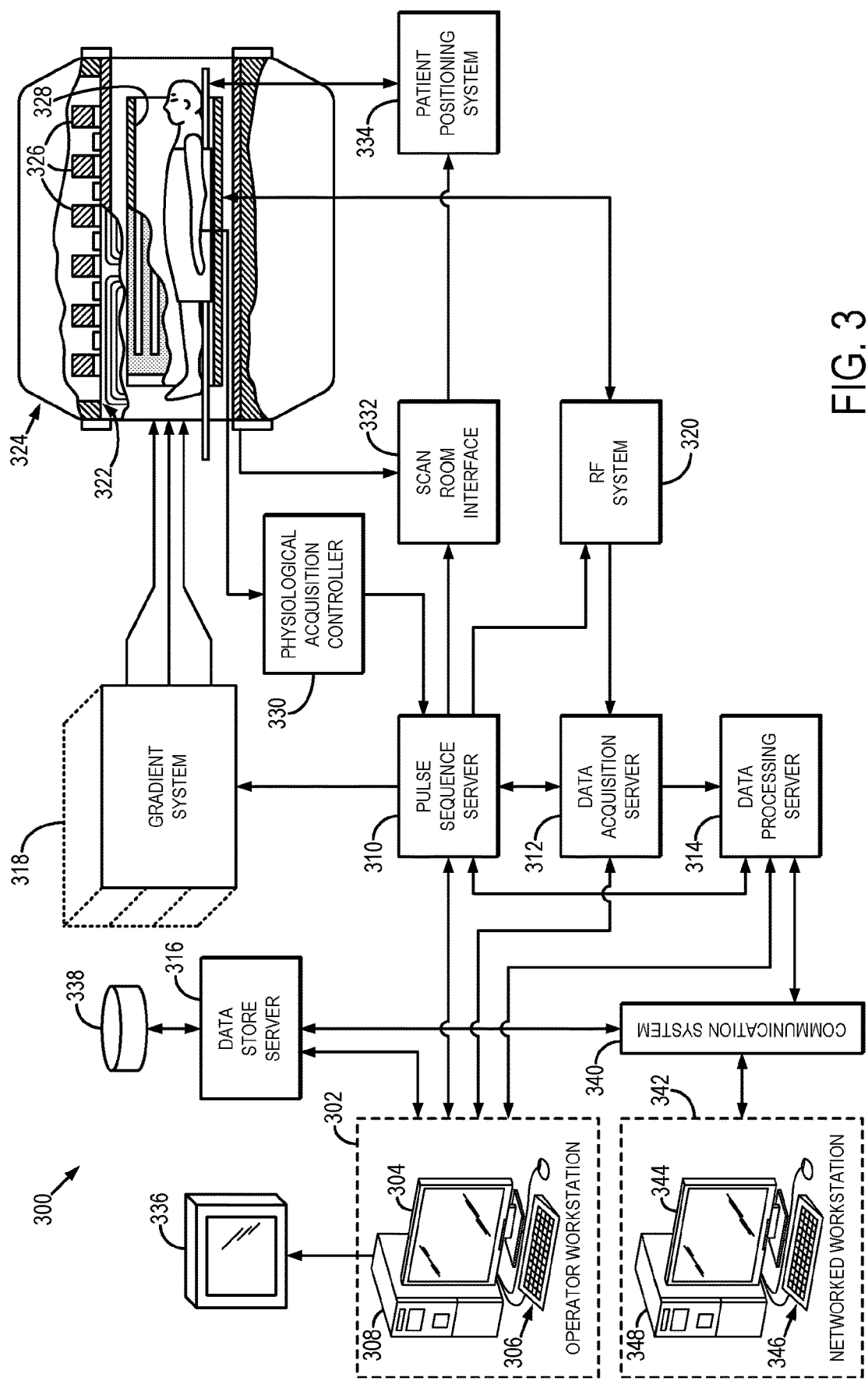
FIG. 3 is a block diagram of an example of a magnetic resonance imaging ("MRI") system.

Referring particularly now to FIG. 3, an example of a magnetic resonance imaging ("MRI") system 300 is illustrated. The MRI system 300 includes an operator workstation 302, which will typically include a display 304; one or more input devices 306, such as a keyboard and mouse; and a processor 308. The processor 308 may include a commercially available programmable machine running a commercially available operating system. The operator workstation 302 provides the operator interface that enables scan prescriptions to be entered into the MRI system 300. In general, the operator workstation 302 may be coupled to four servers: a pulse sequence server 310; a data acquisition server 312; a data processing server 314; and a data store server 316. The operator workstation 302 and each server 310, 312, 314, and 316 are connected to communicate with each other. For example, the servers 310, 312, 314, and 316 may be connected via a communication system 340, which may include any suitable network connection, whether wired, wireless, or a combination of both. As an example, the communication system 340 may include both proprietary or dedicated networks, as well as open networks, such as the internet.

The pulse sequence server 310 functions in response to instructions downloaded from the operator workstation 302 to operate a gradient system 318 and a radiofrequency ("RF") system 320. Gradient waveforms necessary to perform the prescribed scan are produced and applied to the gradient system 318, which excites gradient coils in an assembly 322 to produce the magnetic field gradients $G_x$, $G_y$, and $G_z$ used for position encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil (not shown in FIG. 3), in order to perform the prescribed magnetic resonance pulse sequence. Responsive magnetic resonance signals detected by the RF coil 328, or a separate local coil (not shown in FIG. 3), are received by the RF system 320, where they are amplified, demodulated, filtered, and digitized under direction of commands produced by the pulse sequence server 310. The RF system 320 includes an RF transmitter for producing a wide variety of RF pulses used in MRI pulse sequences. The RF transmitter is responsive to the scan prescription and direction from the pulse sequence server 310 to produce RF pulses of the desired frequency, phase, and pulse amplitude waveform. The generated RF pulses may be applied to the whole-body RF coil 328 or to one or more local coils or coil arrays (not shown in FIG. 3).

The RF system 320 also includes one or more RF receiver channels. Each RF receiver channel includes an RF preamplifier that amplifies the magnetic resonance signal received by the coil 328 to which it is connected, and a detector that detects and digitizes the $I$ and $Q$ quadrature components of the received magnetic resonance signal. The magnitude of the received magnetic resonance signal may, therefore, be determined at any sampled point by the square root of the sum of the squares of the $I$ and $Q$ components:

$$M=\sqrt{I^2+Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 310 also optionally receives patient data from a physiological acquisition controller 330. By way of example, the physiological acquisition controller 330 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, such that no data is lost by data overrun. In some scans, the data acquisition server 312 does little more than pass the acquired magnetic resonance data to the data processor server 314. However, as described above, information derived from acquired magnetic resonance data or other imaging modalities, such as optical imaging modalities, can be used to control the further performance of the scan, such as by identifying regions-of-interest where multidimensional signal localization can be used to acquired localized higher quality images. In these instances, the data acquisition server 312 can be programmed to produce such information and convey it to the pulse sequence server 310, in accordance with the methods descried above. As another example, during prescans, magnetic resonance data is acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also be employed to process magnetic resonance signals used to detect the arrival of a contrast agent in a magnetic resonance angiography ("MRA") scan. By way of example, the data acquisition server 312 acquires magnetic resonance data and processes it in real-time to produce information that is used to control the scan.

The data processing server 314 receives magnetic resonance data from the data acquisition server 312 and processes it in accordance with instructions downloaded from the operator workstation 302. In some embodiments, the data processing server 314 can also receive other imaging data acquired with an optical imaging system or a navigation system, such as a surgical navigation system, and process that data in accordance with instructions downloaded from the operator workstation 302. Such processing may include processing the magnetic resonance data or other imaging data to identify one or more regions-of-interest for which a higher quality image is desired, and to determine scan parameters that define how to control the MRI system to acquire data from the one or more region-of-interest. Such processing may also include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 314 are conveyed back to the operator workstation 302 where they are stored. Real-time images are stored in a data base memory cache (not shown in FIG. 3), from which they may be output to operator display 312 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the operator workstation 302. The operator workstation 302 may be used by an operator to archive the images, produce films, or send the images via a network to other facilities.

The MRI system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 302, or in a different facility, such as a different healthcare institution or clinic.

The networked workstation 342, whether within the same facility or in a different facility as the operator workstation 302, may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may be exchanged between the data processing server 314 or the data store server 316 and the networked workstations 342, such that the data or images may be remotely processed by a networked workstation 342. This data may be exchanged in any suitable format, such as in accordance with the transmission control protocol ("TCP"), the internet protocol ("IP"), or other known or suitable protocols.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for adaptive magnetic resonance imaging (MRI) using an MRI system, the steps of the method comprising:
   (a) providing an image of a subject acquired with a medical imaging system;
   (b) identifying a plurality of regions-of-interest (ROIs) in the provided image for which a higher quality image than the provided image is desired;
   (c) determining scan parameters that define how to control the MRI system to acquire data from the plurality of ROIs;
   (d) simultaneously acquiring with the MRI system, data from the plurality of ROIs using the determined scan parameters to control the MRI system to simultaneously acquire magnetic resonance signals from substantially only the plurality of ROIs;
   (e) reconstructing one or more images of the plurality of ROIs from the data acquired in step(d), wherein the one or more reconstructed images depict the plurality of ROIs with a higher image quality than the image provided in step (a); and
   (f) generating a composite image by merging the one or more images reconstructed in step (e) with the image provided in step (a), wherein the image provided in step (a) depicts a full volume and the one Or more images reconstructed in step (e) depict one or more reduced volumes-of-interest that are one or more sub-volumes of the full volume such that the composite image depicts the higher image quality within the one or more reduced volumes-of-interest while retaining large volume context from the full volume.

2. The method as recited in claim 1, wherein the scan parameters determined in step (c) include parameters that define a spatially-tailored RF excitation, and wherein controlling the MRI system to acquire magnetic resonance signals from substantially only the plurality of ROIs includes controlling the MRI system, using the scan parameters, to provide the spatially-tailored RF excitation to substantially only the plurality of ROIs.

3. The method as recited in claim 1, wherein the scan parameters determined in step (c) are associated with adaptive shim coils, and wherein controlling the MRI system to acquire magnetic resonance signals from substantially only the plurality of ROIs includes controlling adaptive shim coils to perturb a magnetic field of the MRI system such that coherent magnetic resonance signal excitation is achieved substantially only in the plurality of ROIs.

4. The method as recited in claim 1, wherein the scan parameters determined in step (c) include scan parameters that define a higher spatial resolution than the spatial resolution of the provided image.

5. The method as recited in claim 1, wherein the scan parameters determined in step (c) include scan parameters that define a higher signal-to-noise ratio (SNR) than the SNR of the provided image.

6. The method as recited in claim 5, wherein the scan parameters include a number of averages (NEX) value.

7. The method as recited in claim 1, wherein step (a) includes providing a plurality of images of the subject, wherein each of the plurality of images depicts a same field-of-view.

8. The method as recited in claim 7, wherein the plurality of images provided in step (a) includes diffusion-weighted magnetic resonance images that were acquired using a number of different diffusion-encoding directions.

9. The method as recited in claim 8, wherein the scan parameters determined in step (c) includes a number of diffusion-encoding directions that is larger than the number of diffusion-encoding directions used to acquire the provided plurality of images.

10. The method as recited in claim 1, wherein generating the composite image includes overlaying the one more images reconstructed in step (e) on the image provided in step (a).

11. The method as recited in claim 1, wherein step (b) includes manually selecting the plurality of ROIs in the provided image.

12. The method as recited in claim 1, wherein step (b) includes processing the provided image to identify the plurality of ROIs.

13. The method as recited in claim 12, wherein processing the provided image includes segmenting the provided image.

14. The method as recited in claim 12, wherein processing the provided image includes identifying the plurality of ROIs based on image intensity or image contrast characteristics in the provided image.

15. The method as recited in claim 1, wherein the image provided in step (a) is a two-dimensional image acquired with an MRI system.

16. The method as recited in claim 1, wherein the image provided in step (a) is a three-dimensional image volume acquired with an MRI system.

17. A method for adaptive magnetic resonance imaging (MRI) using an MRI system, the steps of the method comprising:
（a）providing a plurality of images of a subject acquired with a medical imaging system, wherein each of the plurality of images depicts a same field-of-view, and wherein the plurality of images includes diffusion-weighted magnetic resonance images that were acquired using a first number of different diffusion-encoding directions;
（b）identifying at least one region-of-interest (ROI) in the provided plurality of images for which a higher quality image than the provided image is desired;
（c）determining scan parameters that define how to control the MRI system to acquire data from the at least one ROI, wherein the scan parameters include a second number of diffusion-encoding directions that is larger than the first number of diffusion-encoding directions used to acquire the provided plurality of images;
（d）acquiring with the MRI system, data from the at least one ROI using the determined scan parameters to control the MRI system to acquire magnetic resonance signals from substantially only the at least one ROI;
（e）reconstructing an image of the at least one ROI from the data acquired in step (d), wherein the reconstructed image depicts the ROI with a higher image quality than the image provided in step (a).

18. The method as recited in claim 17, wherein the at least one ROI depicts a region containing at least one of significant fiber crossing, edema, or small fiber bundles.

19. The method as recited in claim 18, further comprising performing diffusion tractography using the data acquired from the at least one ROI in step (d).

* * * * *